(12) United States Patent
Lavoie et al.

(10) Patent No.: US 7,950,298 B2
(45) Date of Patent: May 31, 2011

(54) MOTORIZED BRACELET ASSEMBLY FOR MOVING SENSOR MODULES AROUND A PIPE

(75) Inventors: Eric Lavoie, Montreal (CA); Gilles Rousseau, Anjou (CA)

(73) Assignee: Hydro-Quebec, Montreal (CA)

( * ) Notice: Subject to any disclaimer, the term of this patent is extended or adjusted under 35 U.S.C. 154(b) by 746 days.

(21) Appl. No.: 10/595,788

(22) PCT Filed: Nov. 12, 2004

(86) PCT No.: PCT/CA2004/001956
§ 371 (c)(1),
(2), (4) Date: Oct. 20, 2008

(87) PCT Pub. No.: WO2005/048271
PCT Pub. Date: May 26, 2005

(65) Prior Publication Data
US 2009/0038398 A1 Feb. 12, 2009

(30) Foreign Application Priority Data
Nov. 14, 2003 (CA) .................................... 2449477

(51) Int. Cl.
*G01D 21/00* (2006.01)
(52) U.S. Cl. ..................................... 73/866.5
(58) Field of Classification Search .................. 73/866.5
See application file for complete search history.

(56) References Cited

U.S. PATENT DOCUMENTS

| 4,331,034 | A | 5/1982 | Takeda et al. |
| 6,222,897 | B1 | 4/2001 | Hatley et al. |
| 6,536,283 | B1 | 3/2003 | Hatley |
| 2004/0020298 | A1 | 2/2004 | Siverling et al. |

FOREIGN PATENT DOCUMENTS

| CA | 1174352 | 9/1984 |
| CA | 2097583 | 12/1993 |
| EP | 412396 A2 | 2/1991 |

OTHER PUBLICATIONS

International Search Report.
International Preliminary Examination Report.

*Primary Examiner* — Hezron Williams
*Assistant Examiner* — Rodney T Frank
(74) *Attorney, Agent, or Firm* — Buchanan Ingersoll & Rooney PC (57) ABSTRACT

A motorized bracelet assembly for ultrasonic crack detection in a pipe. The bracelet has a motorized frame adapted for installation around the pipe and a sliding arrangement slideably mounted onto the frame. The sliding arrangement guides a displacement of sensor modules in periphery of the pipe. A first driving device controllably drives the sliding arrangement and thereby displacing the sensor modules in periphery of the pipe at desired operating positions. The bracelet comprises biasing devices for biasing the sensor modules against the pipe and a second driving device for controllably driving the frame along the axial direction of the pipe at a desired operating position.

16 Claims, 8 Drawing Sheets

MOTORIZED BRACELET ASSEMBLY FOR MOVING SENSOR MODULES AROUND A PIPE

FIELD OF THE INVENTION

The present invention relates to pipe inspection equipment and more particularly to a bracelet assembly for moving sensor modules around a pipe, for example for ultrasonic crack detection in pipes used in nuclear power plants.

BACKGROUND

The international patent application published on Jul. 29, 2004 under no. WO 2004/063660 (Lavoie) discloses a motorized bracelet assembly used to move sensors along a pipe. The bracelet assembly has a frame installable around a pipe and a support device holding the sensors. The frame has wheels for moving the frame in an axial direction of the pipe. A flexible transmission device receives a rotational movement and transmits it to a gear box mounted on the frame. The gear box re-directs the rotational movement from the flexible transmission device towards the wheels. This motorized bracelet facilitates the inspection of the thickness of nuclear pipes with respect to the manually displaceable bracelet assembly disclosed in international patent application published on December 2001 under no. WO 0196808 (Lavoie). However, this motorized bracelet assembly is not adapted for crack detection in the pipes. For crack detection, the sensors must be positioned and moved in periphery and in an axial direction of the pipe while being held at an angle with respect to the surface of the pipe. However, none of the bracelet assemblies known in the art is able to achieve such a positioning and displacement of the sensor modules in periphery of the pipe.

SUMMARY OF THE INVENTION

An object of the present invention is to provide a bracelet assembly for detecting cracks and other possible types of flaws in a pipe.

Another object of the present invention is to provide such a bracelet assembly for detecting cracks and other possible flaws near a dimensional change of a pipe.

Another object of the present invention is to provide such a bracelet assembly, which is versatile and which can be used for other types of operations on a pipe.

According to the present invention, there is provided a bracelet assembly for moving sensor modules around a pipe, comprising:

a frame adapted for installation around the pipe, the frame having a circular shape and a pair of circular members spaced apart from each other;

supports adapted to receive the sensor modules;

a sliding arrangement slideably mounted onto the frame and guiding a displacement of the supports in periphery of the pipe, the sliding arrangement comprising attachments spaced apart from one another and receiving the supports in periphery of the pipe, the sliding arrangement comprising a slideable member to which the supports are attached, and a guide member extending on the frame and slideably receiving the slideable member for sliding along a predetermined sliding range of the peripheral course, the guide member being provided on one of the circular members, the slideable member having an arc shape and extending between the circular members, one of the guide member and the slideable member having elongated grooves extending concentrically with respect to the peripheral course, the other of the guide member and the slideable member having pins engaging in the grooves;

a first driving means for controllably driving the sliding arrangement and thereby displacing the supports in periphery of the pipe at desired operating positions;

biasing means for biasing the sensor modules against the pipe;

wheel arrangements distributed around the frame and projecting therefrom for engagement with the pipe and displacement of the frame along an axial direction of the pipe; and a second driving means for controllably driving the wheels in rotation and thereby displacing the frame along the axial direction of the pipe at a desired operating position.

BRIEF DESCRIPTION OF THE DRAWINGS

These and other objects and advantages of the invention will become apparent upon reading the detailed description and upon referring to the drawings in which.

DESCRIPTION OF PREFERRED EMBODIMENTS

Figure 1:
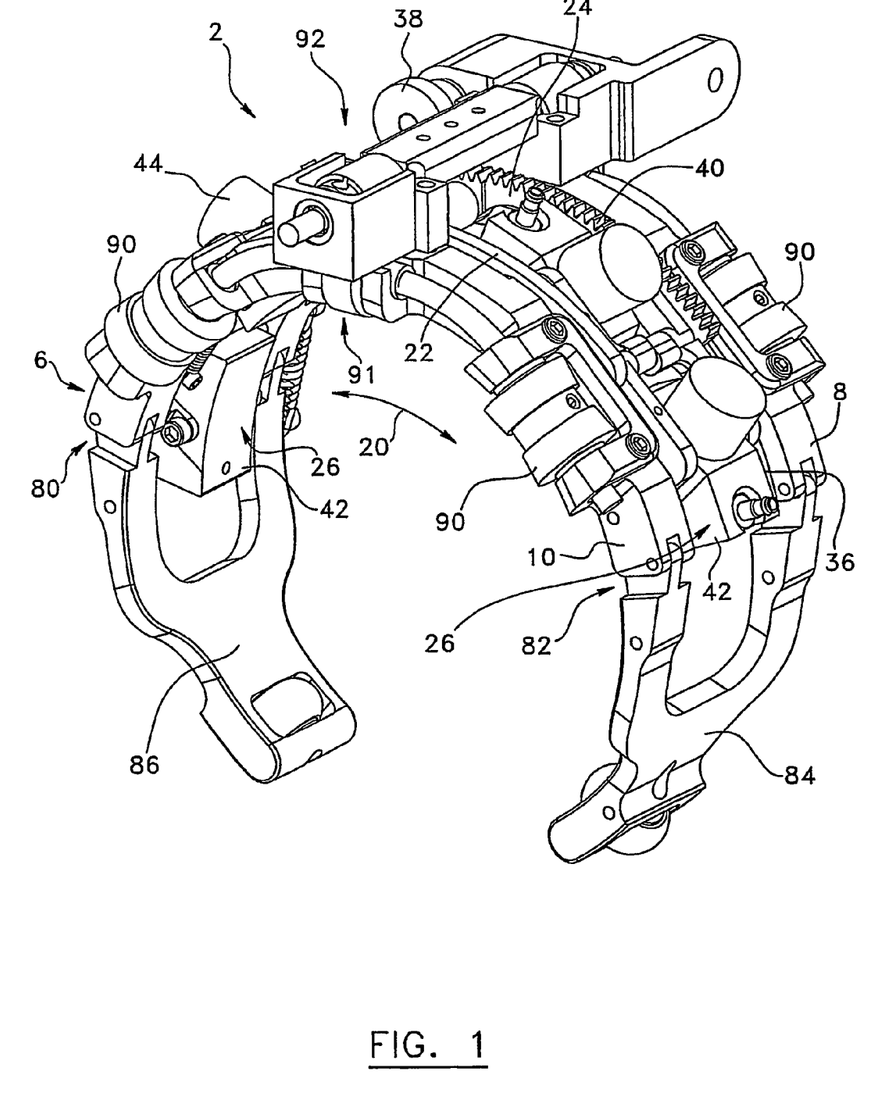
FIG. 1 is a perspective view of a bracelet assembly with inside sensor modules according to the present invention.
Figure 2:
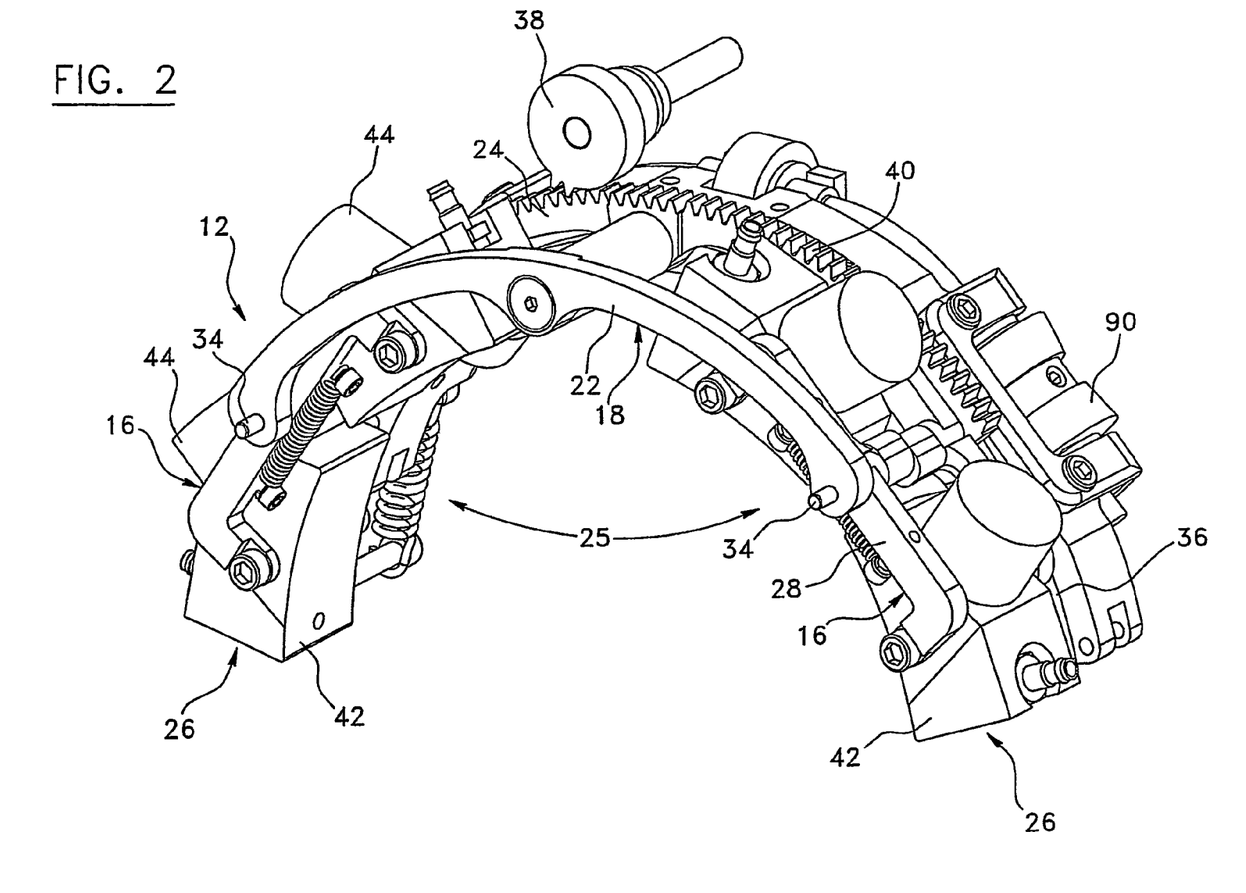
FIG. 2 is a perspective view of a sliding arrangement of a bracelet assembly according to the present invention.
Figure 10:
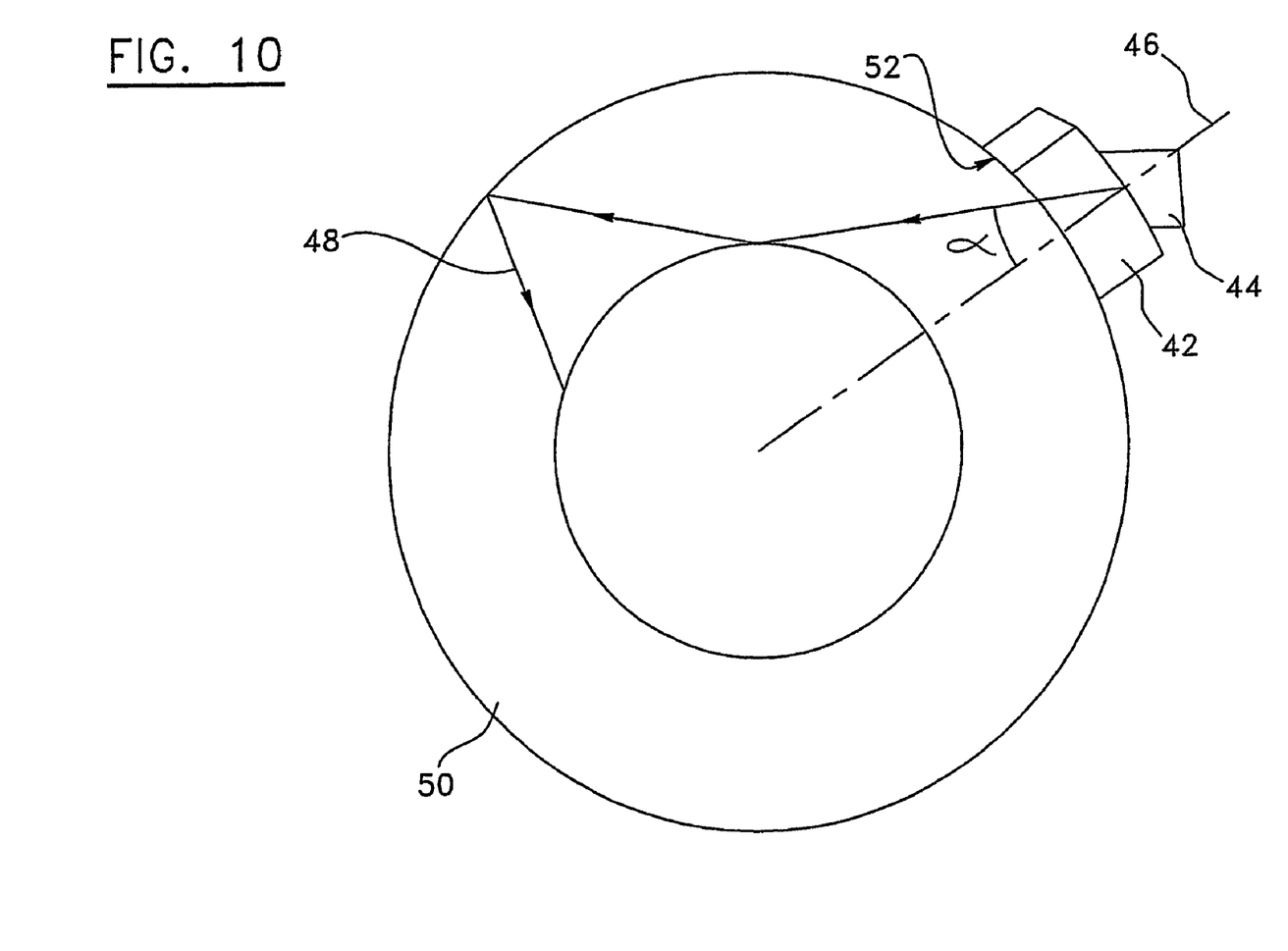
FIG. 10 is a schematic view of an ultrasonic beam traveling within a wall of the pipe.

Referring to FIGS. 1 and 2, there is shown a bracelet assembly 2 according to the present invention, for ultrasonic inspection of pipes, such as the pipe 50 shown in FIG. 10, used for example in CANDU power plants. The bracelet assembly 2 may also be used for inspection of other types of pipes which are hard to reach or for any other pipes where motorized inspection is desired. The bracelet assembly may be adapted for specific inspection needs, such as inspection of graylock welds, 360 degrees inspection of the pipes, etc.

The bracelet assembly 2 has a frame 6 adapted for installation around the pipe. The frame 6 has a pair of circular members 8,10 spaced apart from each other, so that the frame 6 exhibits a circular shape. The shape as such of the frame 6 is not critical, provided that it takes little space and is installable around the pipe (at least over a major part of its perimeter, unless a special attachment is used to hold the bracelet around the pipe). Preferably, the shape of the frame 6 adapts to the shape of the pipes, especially at the level of an elbow section of the pipe where the pipe may have an oval shape.

A sliding arrangement 12 (better shown in FIG. 2) is mounted onto the frame 6 for slideably guiding supports 16 along a peripheral course 20 around the pipe. The slidings arrangement 16 has attachments 25 spaced apart from one another and receiving the supports 16 in periphery of the pipe. As illustrated, the sliding arrangement 12 has a slideable member 18 having a pair of curved arms 22,24, so that to the slideable member 18 exhibits an arc of a hoop shape. The curved arms 22,24 are spaced from one another and extend between the circular members 8,10 of the frame 6.

Pins 34 projecting from each ends of the curved arms 22,24 engage in grooves 36 extending concentrically with respect to the peripheral course 20 on opposite facing sides of the circular members 8,10. The grooves 36 are used as a guide member receiving the slideable member 18 for sliding along a predetermined sliding range of the peripheral course 20. A projecting flange (not shown) extending concentrically with respect to the peripheral course 20 on each of the curved arms 22,24 may also be used instead of the pins 34 to engage the grooves 36.

It is worth noting that the pins 34 may instead be located on the circular members 8,10 and the grooves 36 may be located along a length of the curved arms 22,24.

Figure 3:
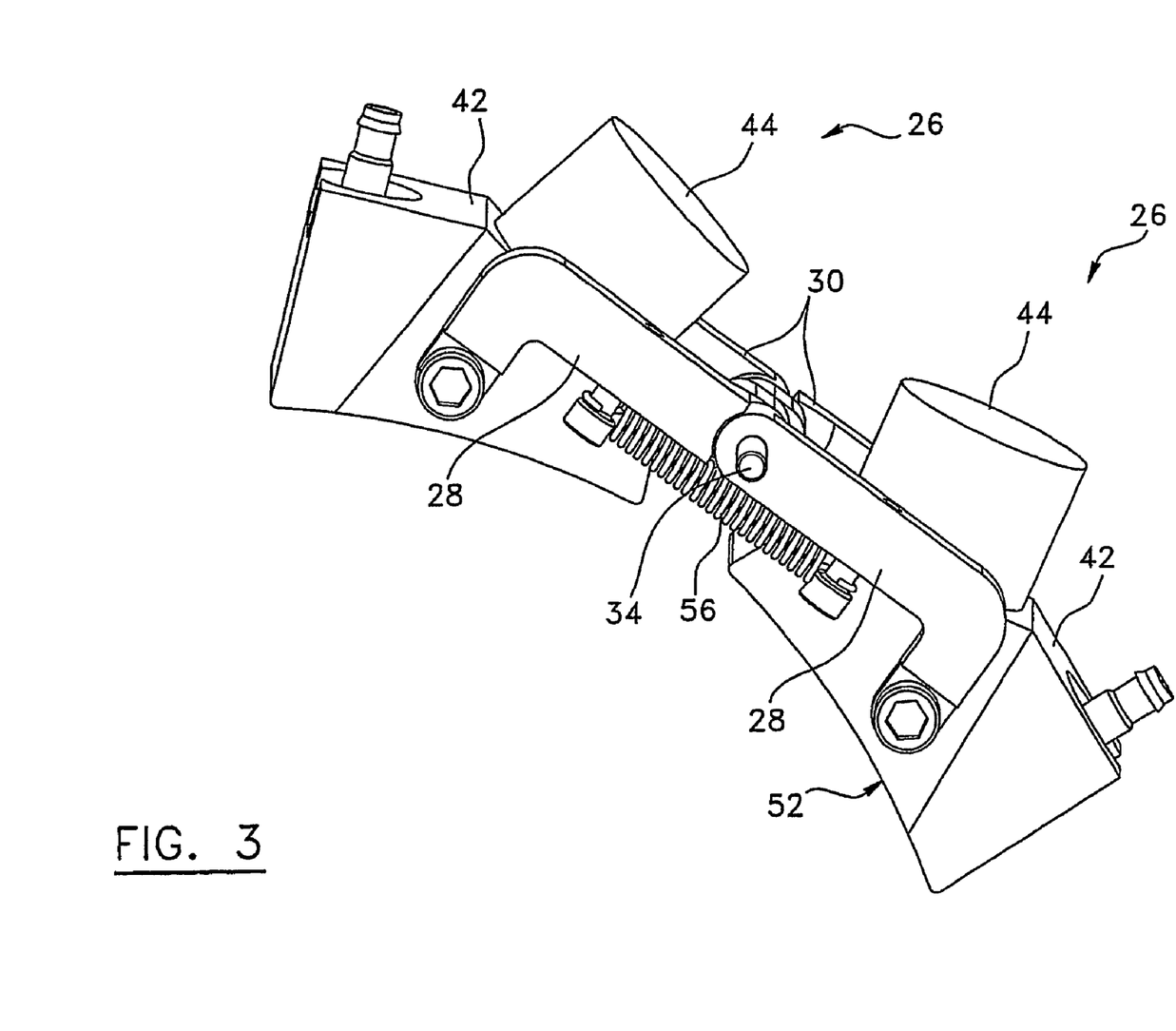
FIG. 3 is a perspective view of a support for sensor modules according to the present invention.

As illustrated in FIG. 3, sensor modules 26 are supported by a pair of arms 28,30 connected to a common pivot point, such as formed by an elongated connecting rod extending transversally between the curved arms 22,24 and providing the pins 34.

Referring back to FIG. 2, although the pins 34 are conveniently extensions of the connecting rod, they could be located at different positions along the length of the curved arms 22,24 if desired.

As shown in FIGS. 1 and 2, a first driving device formed of a driving pinion 38 mounted onto the frame 6 and engaging with an elongated rack 40 extending along a length of the slideable member 18, controllably drives the sliding arrangement 12 to move the supports 16 in periphery of the pipe at desired operating positions. Together, the pinion 38 and the rack 40 form a rack-and-pinion gear operable for producing a reciprocating motion of the sensor modules 26 along the peripheral course 20.

Referring again to FIG. 3, the sensor modules 26 may be formed of wedges 42 and ultrasonic transducers 44 used to detect cracks and flaws in the pipe. The transducers 44 are mounted on the wedges 42 at a predetermined angle with respect to the peripheral surface of the pipe to guide ultrasonic beams 48 of the transducers 44 into the wall 50 of the pipe, as shown in FIG. 10. The wedges 42 may be arranged to guide the ultrasonic beams 48 at other angles within the wall 50 of the pipe. The wedges 42 have bottom surfaces 52 matching an outer peripheral surface of the pipe and they are pivotally attached to the pair of arms 28,30.

Referring to FIGS. 1 to 3, in the illustrated case, there are two pairs of sensor modules 26 connected to the slideable member 18 through the supports 16 located at each end of the slideable member 18. Each pair of sensor modules 26 is formed of two wedge and ultrasonic transducer assemblies pivotably mounted next to each other on the pair of arms 28,30 of the supports 26. The two assemblies are mounted in a back to back type of configuration to direct their respective beam in opposite directions. The driving pinion 38 (shown in FIG. 2) drives the slideable member 18 along the peripheral course 20 to cover the circumference of the pipe.

To insure that the sensor modules 26 stay in contact with the peripheral surface of the pipe, the wedges 42 of a same pair of sensor modules 26 are linked together by a return spring element 56 located at a lower level than the connecting rod, thereby pushing the wedges 42 against the peripheral surface of the pipe.

Figure 4:
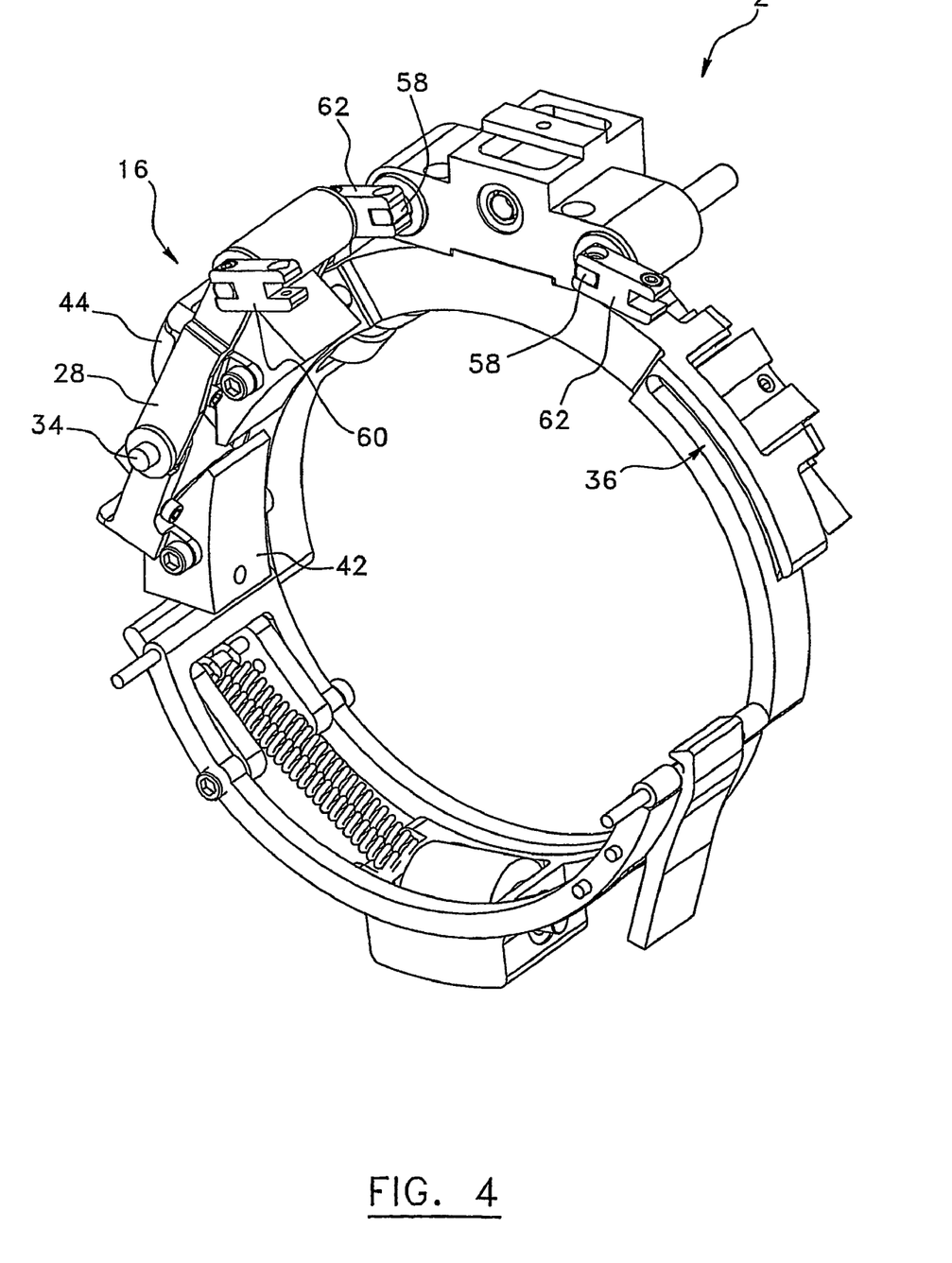
FIG. 4 is a perspective view of a reciprocating arrangement of a bracelet assembly according to the present invention.

Referring to FIG. 4, there is shown a bracelet assembly 2 in which the supports 16 are in the form of reciprocating arrangements guided by the sliding arrangement 12 (shown in FIG. 2) for oscillation along the peripheral course 20. In the illustrated case, the first driving device has rotating shafts 58 mounted on the frame 6 and linked together, e.g. with a linking belt (not shown). The supports 16 have ends provided with connecting rods 60,62 pivotably attached to the rotating shafts 58. The rotary shafts 58 produce reciprocating motions of the supports 16, as required for crack detection.

Figure 5:
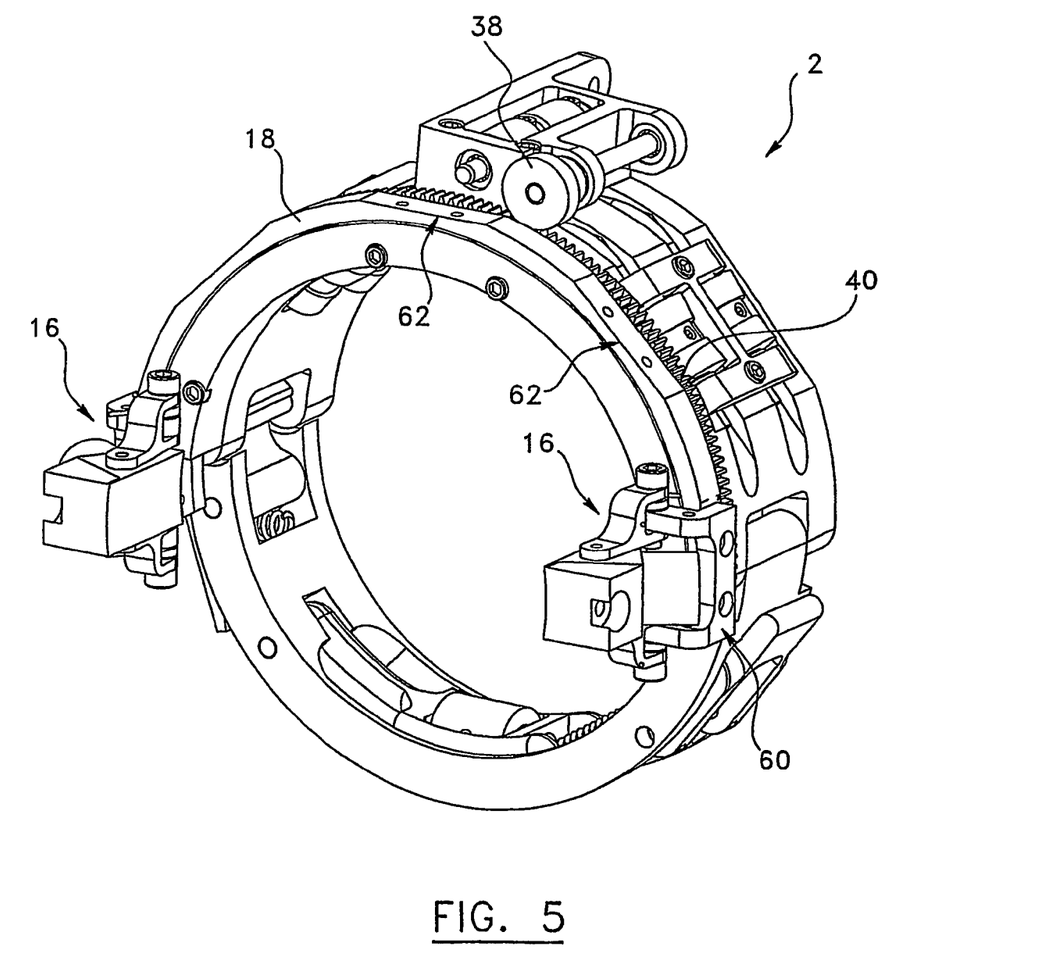
FIG. 5 is a perspective view of another bracelet assembly with outside sensor modules according to the present invention.
Figure 6:
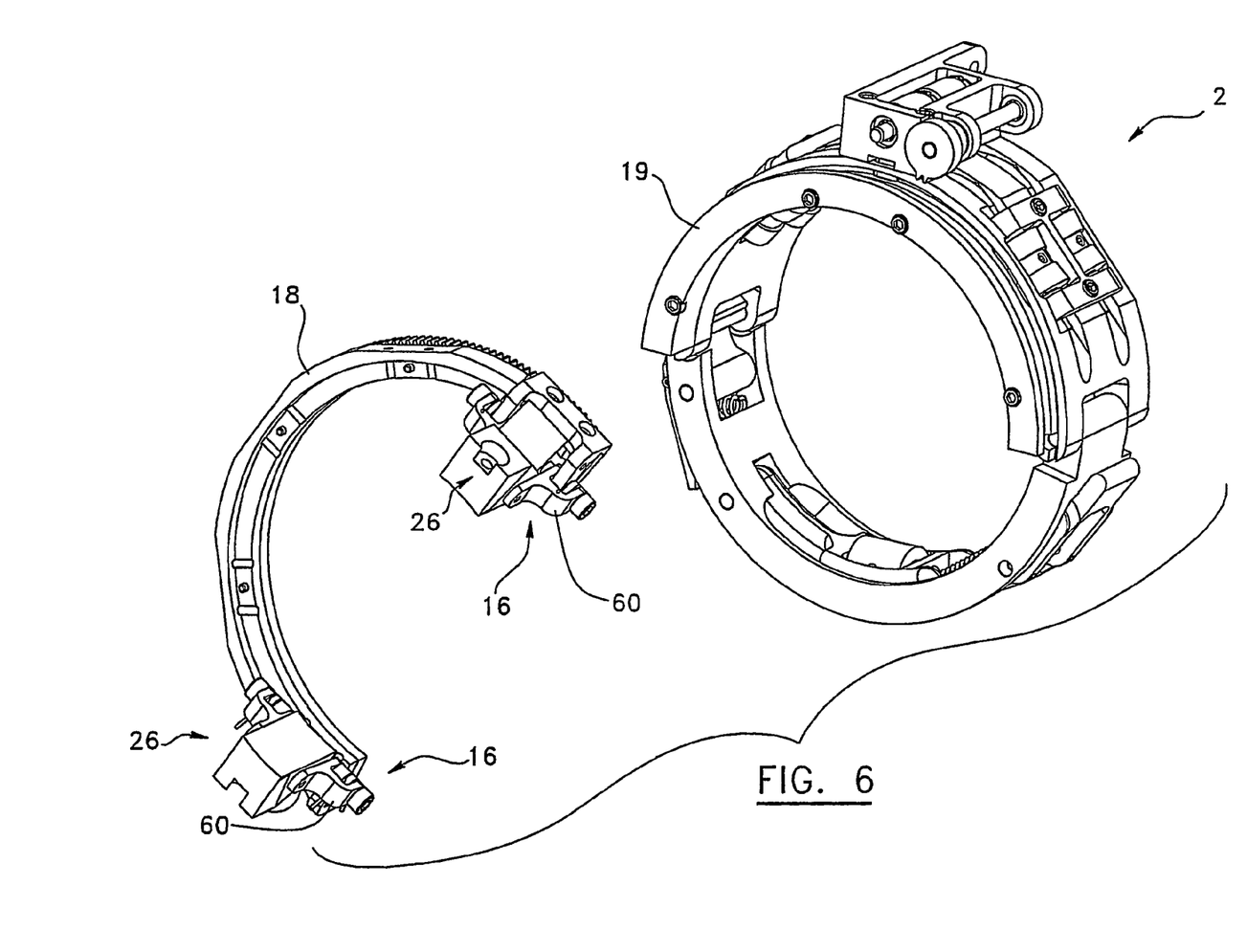
FIG. 6 is a perspective view of a sliding arrangement of a bracelet assembly of the type shown in FIG. 5.

Referring to FIGS. 5 and 6, there is shown another bracelet assembly 2 according to the present invention, which is particularly adapted for inspection near a weld or other dimensional change in the pipe. In this bracelet assembly 2, the slideable member 18 extends on a guide member 19 (shown in FIG. 6) mounted on a front side of the frame 6 around the pipe. The slideable member 18 preferably exhibits an arc of a hoop shape. One support 16 is mounted at each end of the slideable member 18 and extends away from the front side of the frame 6. The sensor modules 26 may be located at an angle of 180 degrees from each other. According to the configuration of the sliding arrangement 12 (shown in FIG. 2), the slideable member 18 can rotate 180 degrees around the pipe to allow the sensor modules to cover all the circumference of the pipe. It is worth noting that the bottom surfaces 52 (shown in FIG. 3) of the wedges 42 (shown in FIG. 3) are contoured to match the peripheral surface of the pipe.

As previously mentioned, the bracelet assembly shown in FIGS. 5 and 6 is suitable for detection near a weld since the sensor modules 26 are extending away from the frame 6 and not between the frame 6; as shown in FIG. 1. The sensor modules 26 (shown in FIG. 3) may thus be positioned closer to the feature to inspect.

Figure 7:
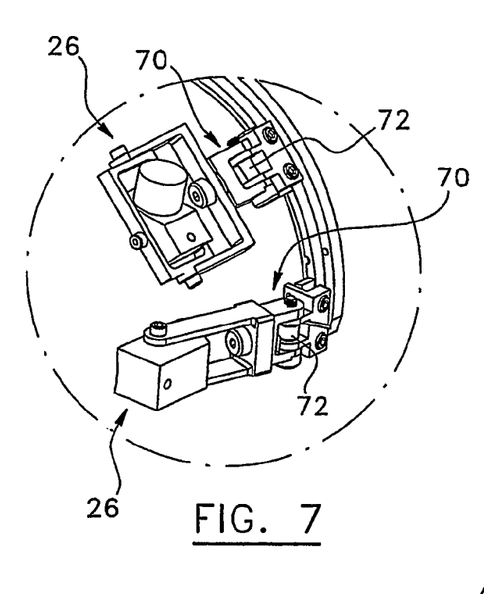
FIGS. 7, 8 and 9 are perspective views of support assemblies for a bracelet assembly of the type shown in FIG. 5.
Figure 8:
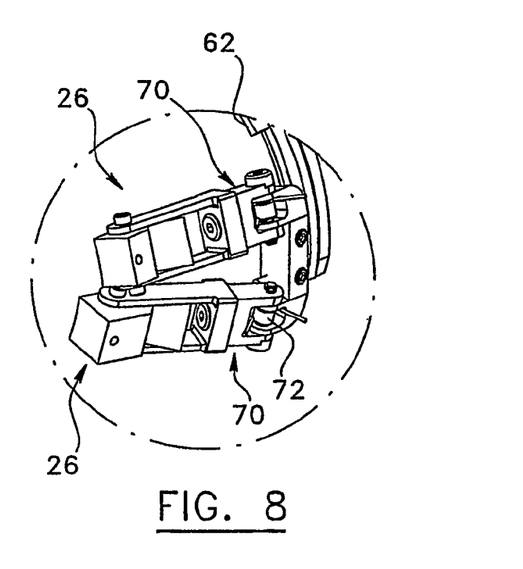
Figure 9:
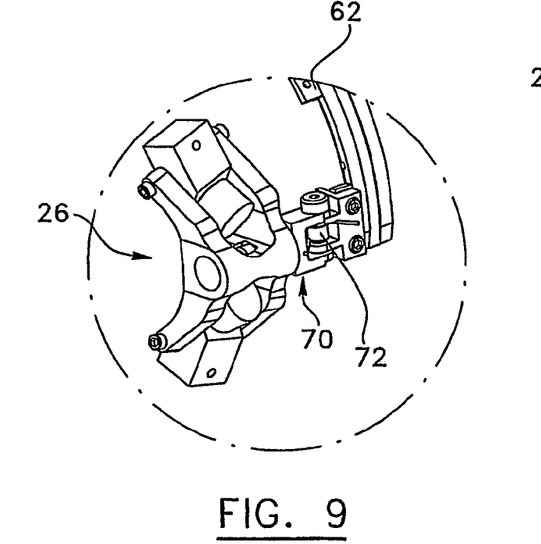

The supports 16 may be mounted at different positions along the length of the slideable member 18. Mounting brackets 60 may be used to fasten the supports 16 to receiving surfaces 62 extending along the length of the slideable member 18. As shown in FIGS. 7 to 9, the receiving surfaces 62 may also project from a front side of the slideable member 18. The mounting brackets 60 may be fastened to the receiving surfaces 62 by screws or other kinds of fasteners if desired.

Referring to FIGS. 7 to 9, various types of supports may be used with the bracelet assembly shown in FIGS. 5 and 6. For example, these supports may comprise a pair of arms 70 pivotably mounted to the mounting brackets 60. The sensor modules 26 extend between the pair of arms 70. Instead of using return spring element 56 to bias the wedges 42 against the surface of the pipe, torsion springs 72 extend between the mounting brackets 60 and the pair of arms 70 to keep the wedges 42 against the surface of the pipe. As illustrated, the supports 26 may be adapted to direct the ultrasonic beams 48 in different directions within the wall 50 of the pipe to detect axial and/or circumferential cracks. Of course, any other suitable combination of these supports 16 may also be used.

In all the illustrated bracelet assemblies 2, the frame 6 is provided with wheel arrangements 90 distributed around the frame 6 and projecting therefrom for engagement with the pipe and displacement of the frame 6 along the axial direction of the pipe. The wheel arrangements 90 may be as the ones described in the international patent application no. WO 2004/063660 (Lavoie).

A second driving device, such as a flexible transmission device 91, as shown in FIG. 1, drives the wheel arrangements 90 in rotation to move the frame 6 along the axial direction of the pipe at a desired operating position. The flexible transmission device 91 may receive a rotational movement and transmit it to a gearing device 92 mounted onto the frame 6. The gearing device 92 re-directs the rotational movement from the flexible transmission device towards the wheels The wheels 90 may be magnetized to insure good traction on the pipe and to help keeping the bracelet assembly 2 in position around the pipe in presence of slippery couplant.

One of the advantages of the bracelet is that it may be easily installed and uninstalled around the pipes.

Although preferred embodiments of the present invention have been described in detail hereinabove and illustrated in the accompanying drawings, it is to be understood that the invention is not limited to these precise embodiments and that various changes and modifications may be effected therein without departing from the scope or spirit of the present invention.

Furthermore, as shown in FIG. 1, a closing device may be mounted between two open ends 80,82 of the frame 6 to fasten the bracelet assembly 2 around the pipe. The closing device may be formed of a pair of legs 84, 86 pivotally connected respectively to the open ends 80,82 of the frame 6, and forming complementary extensions thereof. Although not illustrated in FIG. 1, the legs 84,86 may also be connected with each other by a spring element or any other suitable fastener. The closing device may be manually operated and is preferably straightforward to operate, thus requesting very few manipulations from an operator. Other closing devices, such as the ones shown in FIGS. 4 and 5, may be used instead. Also, the bracelet assembly could be made of flexible material so that no closing devices would be needed.

Moreover, instead of a wedge and ultrasonic transducer assembly, the sensor modules may be formed of a non-sensing tool or device, such as an abrasive tool used to process the surface of the pipe. The expression "sensor module" has been used herein for sake of simplicity. But it should be construed as including non-sensing modules as mentioned above.

The compact configuration of bracelet assembly 2 allows it to be used in cramped space.

What is claimed is:

1. A bracelet assembly for moving sensor modules around a pipe, comprising:
    a frame adapted for installation around the pipe, the frame having a circular shape and a pair of circular members spaced apart from each other;
    supports adapted to receive the sensor modules;
    a sliding arrangement slideably mounted onto the frame and guiding a displacement of the supports in periphery of the pipe, the sliding arrangement comprising attachments spaced apart from one another and receiving the supports in periphery of the pipe, the sliding arrangement comprising a slideable member to which the supports are attached, and a guide member extending on the frame and slideably receiving the slideable member for sliding along a predetermined sliding range of the peripheral course, the guide member being provided on one of the circular members, the slideable member having an arc shape and extending between the circular members, one of the guide member and the slideable member having elongated grooves extending concentrically with respect to the peripheral course, the other of the guide member and the slideable member having pins engaging in the grooves;
    a first driving means for controllably driving the sliding arrangement and thereby displacing the supports in periphery of the pipe at desired operating positions;
    biasing means for biasing the sensor modules against the pipe;
    wheel arrangements distributed around the frame and projecting therefrom for engagement with the pipe and displacement of the frame along an axial direction of the pipe; and
    a second driving means for controllably driving the wheels in rotation and thereby displacing the frame along the axial direction of the pipe at a desired operating position.

2. The bracelet assembly according to claim 1, wherein:
    the slideable member has a pair of curved arms spaced from one another and extending between the circular members of the frame, the pins projecting from the curved arms, the grooves extending on opposite sides of the circular arms and facing one another.

3. The bracelet assembly according to claim 2, wherein:
    each of the supports comprises an elongated connecting rod mounted to the curved arms and extending substantially transversally between the curved arms, the connecting rod has opposed ends projecting from the curved arms and engaging in the grooves.

4. The bracelet assembly according to claim 1, wherein:
    the slideable member has an elongated rack extending along a length thereof; and
    the first driving means has a driving pinion mounted onto the frame and engaging with the rack so that the pinion and the rack form a rack-and-pinion gear operable for producing a reciprocating motion of the sensor modules along the peripheral course.

5. The bracelet assembly according to claim 1, wherein:
    the sensor modules comprise ultrasonic transducers and wedges having bottom surfaces matching an outer peripheral surface of the pipe and surfaces receiving the transducers at a predetermined angle with respect to the peripheral surface of the pipe, the wedges being pivotally attached to the supports.

6. The bracelet assembly according to claim 5, wherein each sensor module comprises two wedge and ultrasonic transducers assemblies pivotably mounted next to each other along the peripheral course around the pipe.

7. The bracelet assembly according to claim 5, wherein each support comprises a pair of arms operatively connected to the sliding arrangement and between which one of the sensor modules is pivotally mounted.

8. The bracelet assembly according to claim 6, wherein each support comprises a pair of arms operatively connected to the sliding arrangement and between which the two wedge and ultrasonic transducer assemblies are pivotally mounted.

9. The bracelet assembly according to claim 8, wherein the biasing means comprises a return spring element extending between each wedge of the two wedge and ultrasonic transducer assemblies at a lower level than a pivot point of the wedges.

10. The bracelet assembly according to claim 1, wherein the supports respectively comprise reciprocating arrangements coupled to the first driving means and guided by the sliding arrangement for oscillation along the peripheral course.

11. The bracelet assembly according to claim 10, wherein:
    the first driving means comprises rotating shafts mounted in the frame; and
    the supports have ends provided with connecting rods pivotably attached to the rotating shafts and producing reciprocating motions of the supports.

12. The bracelet assembly according to claim 1, wherein:
    the slideable member extends on a front side of the frame around the pipe; and the supports project from the slideable member away from the front side of the frame.

13. The bracelet assembly according to claim 12, wherein:
each support comprises a mounting bracket removably mounted to the slideable member; and
the slideable member has receiving surfaces extending along a length thereof, the mounting brackets being fastened to the receiving surfaces.

14. The bracelet assembly according to claim 13, wherein the receiving surfaces are extending on a front side of the slideable member around the pipe.

15. The bracelet assembly according to claim 12, wherein:
the supports comprise pair of arms pivotally mounted to the mounting brackets and between which the sensor modules extend; and
the biasing means comprises torsion springs extending between the mounting brackets and the pair of arms.

16. The bracelet assembly according to claim 1, wherein the wheel arrangements comprise magnetized wheels.

\* \* \* \* \*